(12) United States Patent
Gambale

(10) Patent No.: US 6,929,646 B2
(45) Date of Patent: Aug. 16, 2005

(54) IMPLANTABLE BONE FRACTURE REDUCTION APPARATUS HAVING A POLYMERIC APPLICATOR

(75) Inventor: Michael A. Gambale, Hingham, MA (US)

(73) Assignee: Integra Signature Technologies, Inc., Plainsboro, NJ (US)

( * ) Notice: Subject to any disclaimer, the term of this patent is extended or adjusted under 35 U.S.C. 154(b) by 130 days.

(21) Appl. No.: 10/099,505

(22) Filed: Mar. 15, 2002

(65) Prior Publication Data

US 2002/0147453 A1 Oct. 10, 2002

Related U.S. Application Data

(60) Provisional application No. 60/281,562, filed on Apr. 4, 2001.

(51) Int. Cl.[7] .............................................. A61B 17/56
(52) U.S. Cl. ........................................ 606/71; 606/69
(58) Field of Search ............................. 606/71, 69, 99, 606/104, 70, 60, 61; 623/16.11; 40/5; D20/22

(56) References Cited

U.S. PATENT DOCUMENTS 4,263,903 A * 4/1981 Griggs ......................... 606/75
4,923,471 A * 5/1990 Morgan ........................ 606/60
4,927,425 A * 5/1990 Lozier ........................... 606/99
4,959,065 A * 9/1990 Arnett et al. .................. 606/69
D320,414 S * 10/1991 Morgan ....................... D20/22
5,468,242 A * 11/1995 Reisberg ....................... 606/69
5,578,036 A * 11/1996 Stone et al. ................... 606/69
5,718,705 A * 2/1998 Sammarco .................... 606/69
5,782,919 A * 7/1998 Zdeblick et al. ........... 623/17.16
5,997,539 A * 12/1999 Errico et al. .................. 606/61
6,319,257 B1 * 11/2001 Carignan et al. ............. 606/99
6,446,711 B1 * 9/2002 DeGroot et al. ............. 165/149

* cited by examiner

Primary Examiner—Pedro Philogene
(74) Attorney, Agent, or Firm—Tarolli, Sundheim, Covell & Tummino L.L.P.

(57) ABSTRACT

An implantable apparatus (10) for attaching bone fragments in a bone fracture reduction procedure comprises a bone affixation plate (12) and a polymeric applicator (18) having a deflectable portion (22) that is deflectable to engage a portion (16) of the plate to attach the applicator to the plate. The applicator (18) is thereafter deflectable to disengage from the portion (16) of the plate (12) to remove the applicator from the plate. The applicator (18), when attached to the plate (12), enables the plate to be handled and manipulated during the bone fracture reduction procedure. The applicator (18) may includes information (24) for identifying the plate (12).

9 Claims, 1 Drawing Sheet

US 6,929,646 B2

IMPLANTABLE BONE FRACTURE REDUCTION APPARATUS HAVING A POLYMERIC APPLICATOR

This claims the benefit of Provisional Application No. 60/281,562, filed Apr. 4, 2001.

TECHNICAL FIELD

The present invention relates to an implantable bone fracture reduction apparatus that includes a polymeric applicator. The polymeric applicator is removably attached to a bone affixation plate and may include identifying information about the bone affixation plate.

BACKGROUND OF THE INVENTION

A known bone fracture reduction device is disclosed in U.S. Pat. No. 4,923,471, which is incorporated herein by reference in its entirety. The known bone fracture reduction device includes a metallic plate. A number of openings extend through the plate. Each of the openings is sized for receiving a biocompatible bone screw for affixing a portion of the plate to bone at a bone fracture site.

The known bone fracture reduction device also includes a metallic identification (ID) tag. The ID tag includes information identifying the plate. Such information may include a lot number, screw sizes for use in the openings of the plate, and a product number. Such identifying information is useful for tracking the plate during a surgical procedure. The ID tag also includes an elongated, metallic stem portion that connects to the plate.

During a surgical procedure, the ID tag may be used to position the plate in a desired position relative to the bone fracture. After the plate is affixed to bone using the bone screws, the ID tag is removed from the plate by severing the stem portion from the plate. To sever the stem portion of the ID tag from the plate, the stem portion is either cut or is twisted until severed from the plate.

A consequence of severing the stem portion of the ID tag from the plate is that a burr of metal can remain attached to the plate in the location where the stem portion was removed. A bone fracture reduction apparatus which includes a plate and a removable ID tag that will not leave a burr on the plate is desirable.

SUMMARY OF THE INVENTION

The present invention is an implantable apparatus for attaching bone fragments in a bone fracture reduction procedure. The apparatus comprises a bone affixation plate and a polymeric applicator having a deflectable portion that is deflectable to engage a portion of the plate to attach the applicator to the plate. The applicator is thereafter deflectable to disengage from the portion of the plate to remove the applicator from the plate. The applicator, when attached to the plate, enables the plate to be handled and manipulated during the bone fracture reduction procedure.

In accordance with one aspect of the invention, the applicator further includes means for identifying the plate.

In accordance with another aspect of the invention, the deflectable portion of the applicator attaches to the plate with a snap fit.

In accordance with yet another aspect of the invention, removal of the applicator from the plate leaves no residue of the applicator on the plate.

In accordance with still another aspect of the invention, the deflectable portion includes first and second legs that together form a receptacle for receiving the portion of the plate. The first and second legs extend from a main body portion of the applicator and being resiliently deflectable away from one another.

BRIEF DESCRIPTION OF THE DRAWINGS

The foregoing and other features of the present invention will become apparent to those skilled in the art to which the present invention relates upon reading the following summary with reference to the accompanying drawings, in which.

DESCRIPTION OF EMBODIMENTS

Figures 1, 2:
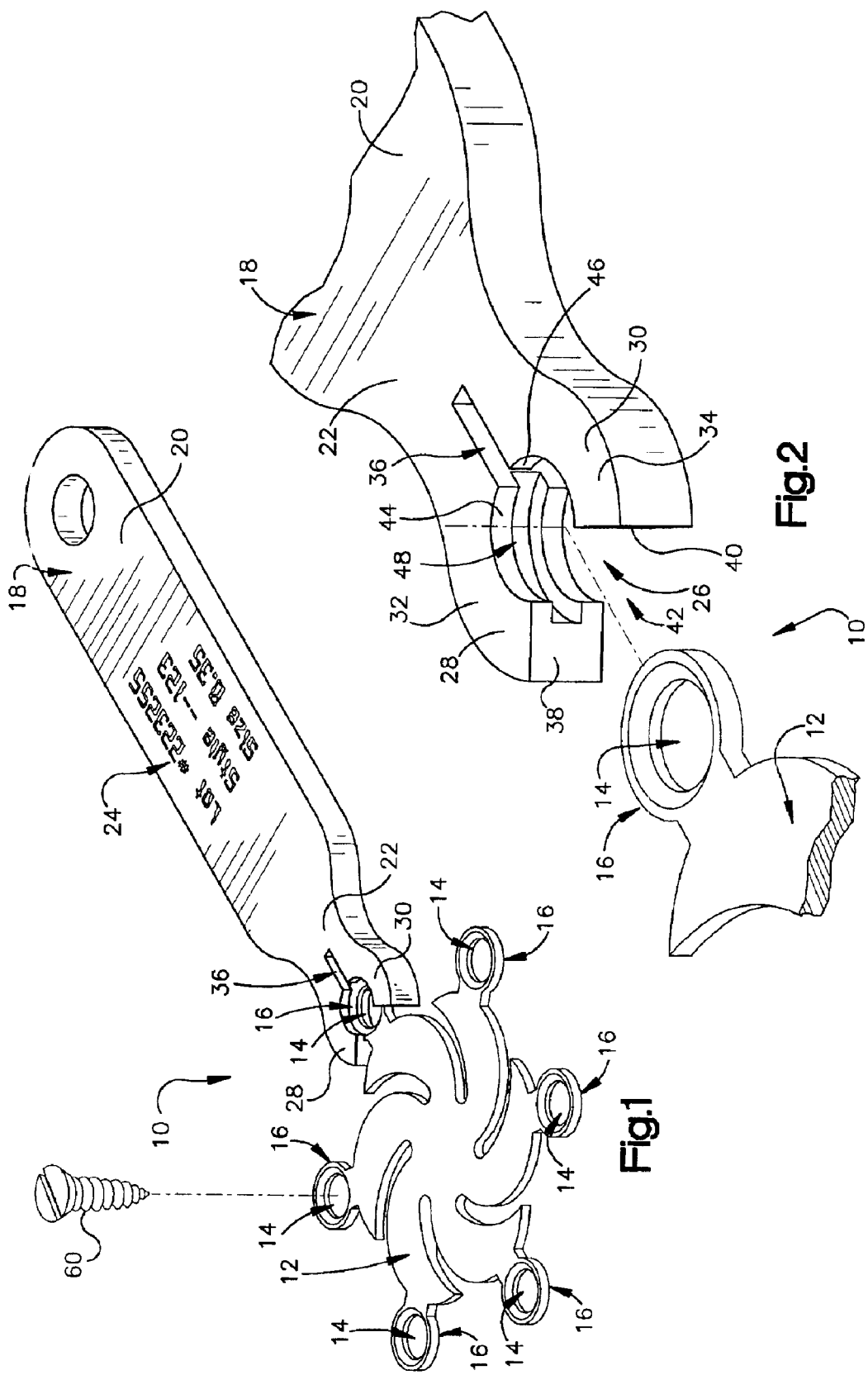
FIG. 1 is a perspective view of an implantable bone fracture reduction apparatus constructed in accordance with the present invention.
FIG. 2 is a perspective view of a portion of the apparatus of FIG. 1 wherein a plate of the apparatus is separated from an applicator of the apparatus.

An implantable bone fracture reduction apparatus 10 constructed in accordance with the present invention is illustrated in FIG. 1. The apparatus 10 includes a thin, malleable plate 12 made of a biocompatible material, such as titanium. The plate 12, commonly referred to as a "mesh," could alternatively be made from other metallic materials or from non-metallic materials. The plate 12 is for fixation of a bone fracture and includes at least two openings 14, six of which are shown in FIG. 1, that extend through the plate 12. Each of the openings 14 extends through a circular lobe 16 of the plate 12. Each of the openings 14 is designed to receive a bone screw, such as the bone screw 60 shown in FIG. 1. It should be understood that the present invention could be adapted for any of the wide variety of the known plate configurations that are commercially available and that include one or more openings for bone screws.

The implantable bone fracture reduction apparatus 10 further includes a polymeric applicator 18. The applicator 18 includes a handle portion 20 and a deflectable portion 22. The handle portion 20 includes means 24 for identifying the plate 12 to which the applicator 18 is attached. The identifying means 24 may include a lot number, a product number, bone screw sizes, plate configuration, and any other identifying information. Additionally, the applicator 18 may be color coded for identifying information about the plate 12, such as bone screw sizes.

In addition to providing information identifying the plate 12, the handle portion 20 of the applicator 18 also provides means for handling and manipulating the plate 12 during the fracture reduction procedure. When the applicator 18 is attached to the plate 12, the handle portion 20 permits a user of the apparatus 10 to adjust the position of the plate 12 by moving the handle portion 20 of the applicator 18.

The handle portion 20 illustrated in FIG. 1 is flat and axially elongated. Alternative embodiments of the handle portion 20 may be curved or bent at an angle, or may have gripping features. Further, the handle portion 20 may have a flexible polymer outer layer with a bendable supporting structure, such as a metallic wire, inside the outer layer.

As shown in FIG. 2, the deflectable portion 22 of the applicator 18 includes a receptacle 26 that is sized and shaped for receiving and engaging one of the lobes 16 of the plate 12. The receptacle 26 illustrated in FIG. 2 is semi-circular and is formed from a pair of legs 28 and 30 of the deflectable portion 22 of the applicator 18. A first leg 28 is formed by a first arched portion 32 and forms a first part of the receptacle 26. A second leg 30 is formed from a second arched portion 34 and forms a second part of the receptacle 26. A short axially extending slot 36 separates the first arched portion 32 from the second arched portion 34 on the deflectable portion 22 of the applicator 18. The first arched portion 32 of the first leg 28 extends in a direction opposite to the second arched portion 34 of the second leg 30 so that the first and second legs 28 and 30 collectively form the semi-circular receptacle 26. Terminal ends 38 and 40 of the first and second arched portions 32 and 34, respectively, are separated by a space 42 through which the lobe 16 of the plate 12 passes when the applicator 18 is being attached to the plate 12. An inner surface 44 and 46 of each arched portion 32 and 34 includes a circumferentially extending groove 48 for receiving the lobe 16 of the plate 12.

The deflectable portion 22 of the applicator 18 engages and attaches to the lobe 16 of the plate 12 with a snap fit. To attach the applicator 18 to the plate 12, the deflectable portion 22 of the applicator is aligned with the lobe 16 of the plate such that the terminal ends 38 and 40 of the arched portions 32 and 34 contact t-.he respective lobe 16. The applicator 18 is then pressed toward the plate 12 so that the first and second legs 28 and 30 of the deflectable portion 22 of the applicator 18 deflect away from one another and the lobe 16 of the plate 12 is received in the receptacle 26. The axial slot 36 separating the first and second legs 28 and 30 enables the deflection of the legs 28 and 30 away from one another.

When received in the receptacle 26 of the deflectable portion 22 of the applicator 18, the lobe 16 of the plate 12 seats in the groove 48 on the inner surface 44 and 46 of each leg 28 and 30. Once the lobe 16 is received in the receptacle 26, the legs 28 and 30 snap back to their non-deflected positions (shown in FIG. 1) and clamp the lobe 16 of the plate 12 to secure the applicator 18 to the plate 12.

During a surgical procedure, the applicator 18 allows a user of the apparatus 10 to handle and manipulate the plate 12 to a desired position relative to a bone fracture. After the plate 12 is affixed to bone using bone screws, the applicator 18 is removed from the plate 12 by simply pulling the applicator off of the plate 12. When the applicator 18 is pulled relative to the plate 12, the legs 28 and 30 of the deflectable portion 22 of the applicator deflect away from one another as the receptacle 26 of the deflectable portion disengages from the lobe 16 of the plate 12. Removal of the applicator 18 leaves behind only the plate 12, i.e., no residue of the applicator 18, such as a burr, is left on the plate 12.

From the above description of the invention, those skilled in the art will perceive improvements, changes and modifications. For example, it should be understood that the applicator disclosed above could be modified to engage a variety of structural features found in various bone plates, such as the upper and lower surface surfaces of a plate or an opening in the plate. Such improvements, changes and modifications within the skill of the art are intended to be covered by the appended claims.

Having described the invention, I claim:

1. An implantable apparatus for attaching bone fragments in a bone fracture reduction procedure, said apparatus comprising:

a bone affixation plate; and a polymeric applicator having a deflectable portion that is deflectable to engage a portion of said plate and attach said applicator to said plate with a snap fit, said deflectable portion being thereafter deflectable to disengage from said portion of said plate to remove said applicator from said plate and leave no residue of said applicator on said plate;

said applicator, when attached to said plate, enabling said plate to be handled and manipulated during the bone fracture reduction procedure.

2. The apparatus of claim 1 wherein said applicator further including means for identifying said plate.

3. The apparatus of claim 1 wherein said deflectable portion includes first and second legs that together form a receptacle for receiving said portion of said plate, said first and second legs extending from a main body portion of said applicator and being resiliently deflectable away from one another.

4. The apparatus of claim 3 wherein said first leg includes a first groove and said second leg includes a second groove, said portion of said plate seating in said first and second grooves when said applicator is attached to said plate.

5. The apparatus of claim 3 wherein said first and second legs are separated by an axially extending slot, said axially extending slot enabling said first and second legs to deflect away from one another.

6. An implantable apparatus for attaching bone fragments in a bone fracture reduction procedure, said apparatus comprising:

a thin malleable bone affixation plate formed of a biocompatible material, said plate having at least two openings extending through said plate, each of said at least two openings for receiving a bone screw to be driven into a bone fragment to affix said plate to the bone fragment; and a polymeric applicator having a deflectable portion that is deflectable for receiving a portion of said plate and attach said applicator to said plate with a snap fit, said deflectable portion being thereafter deflectable to release said portion of said plate to remove said applicator from said plate and have no residue of said applicator on said plate;

said applicator, when attached to said plate, enabling said plate to be handled and manipulated during the bone fracture reduction procedure;

said applicator further including means for identifying said plate.

7. The apparatus of claim 6 wherein said deflectable portion includes first and second legs that together form a receptacle for receiving said portion of said plate, said first and second legs extending from a main body portion of said applicator and being resiliently deflectable away from one another.

8. The apparatus of claim 7 wherein said first leg includes a first groove and said second leg includes a second groove, said portion of said plate seating in said first and second grooves when said applicator is attached to said plate.

9. The apparatus of claim 7 wherein said first and second legs are separated by an axially extending slot, said axially extending slot enabling said first and second legs to deflect away from one another.

* * * * *